United States Patent
Hidaka et al.

(10) Patent No.: US 11,980,341 B2
(45) Date of Patent: May 14, 2024

(54) ENDOSCOPE TREATMENT TOOL

(71) Applicant: OLYMPUS CORPORATION, Tokyo (JP)

(72) Inventors: Yuya Hidaka, Tokyo (JP); Chika Miyajima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 592 days.

(21) Appl. No.: 17/197,285

(22) Filed: Mar. 10, 2021

(65) Prior Publication Data

US 2021/0196104 A1    Jul. 1, 2021

Related U.S. Application Data

(63) Continuation of application No. PCT/JP2018/033939, filed on Sep. 13, 2018.

(51) Int. Cl.
*A61B 1/00* (2006.01)
*A61B 17/00* (2006.01)
(Continued)

(52) U.S. Cl.
CPC ...... *A61B 1/00101* (2013.01); *A61B 1/00087* (2013.01); *A61B 1/00089* (2013.01);
(Continued)

(58) Field of Classification Search
CPC .............. A61B 1/0008; A61B 1/00087; A61B 1/00101; A61B 1/0014; A61B 17/00234;
(Continued)

(56) References Cited

U.S. PATENT DOCUMENTS

2002/0163629 A1  11/2002  Switkes et al.
2005/0049454 A1   3/2005  Ouchi
(Continued)

FOREIGN PATENT DOCUMENTS

EP  1834599 A1  9/2007
EP  1886634 A1  2/2008
(Continued)

OTHER PUBLICATIONS

Japanese Office Action dated Jul. 19, 2021 received in 2020-546620.
(Continued)

*Primary Examiner* — Michael J Carey
*Assistant Examiner* — Timothy Tuan Luu
(74) *Attorney, Agent, or Firm* — Scully, Scott, Murphy & Presser, P.C.

(57) ABSTRACT

An endoscope treatment tool includes: a cylindrical distal-end member to be attached to a distal end of an endoscope; a grasping tool that is provided at an outer side surface of the endoscope along a longitudinal axis of the endoscope, that grasps biological tissue, and that is movable in a first direction perpendicular to the longitudinal axis in a state in which the biological tissue is grasped; an electrode that is disposed so as to protrude forward with respect to a distal end of the distal-end member; and an electrode driving portion that is configured to move the electrode in the first direction.

8 Claims, 9 Drawing Sheets

(51) Int. Cl.
*A61B 17/29* (2006.01)
*A61B 18/14* (2006.01)

(52) U.S. Cl.
CPC .... *A61B 1/00137* (2013.01); *A61B 17/00234* (2013.01); *A61B 17/29* (2013.01); *A61B 18/1445* (2013.01); *A61B 2017/00296* (2013.01)

(58) Field of Classification Search
CPC ............ A61B 17/29; A61B 18/1445; A61B 2018/00601; A61B 2018/00982; A61B 2018/144; A61B 1/00137; A61B 18/14; A61B 2018/1405; A61B 2018/1407; A61B 2018/141; A61B 2018/1475; A61B 1/00089
See application file for complete search history.

(56) References Cited

U.S. PATENT DOCUMENTS

| | | | |
|---|---|---|---|
| 2007/0038022 A1 | 2/2007 | Nakao | |
| 2007/0203397 A1* | 8/2007 | Kanzaki | A61B 1/00089 600/179 |
| 2008/0125803 A1 | 5/2008 | Sadamasa et al. | |
| 2008/0132759 A1 | 6/2008 | Miyamoto et al. | |
| 2008/0249354 A1 | 10/2008 | Muyari et al. | |
| 2016/0029875 A1* | 2/2016 | Okada | A61B 1/00101 600/107 |
| 2017/0105797 A1* | 4/2017 | Mikkaichi | A61B 18/14 |
| 2019/0069946 A1* | 3/2019 | Löffler | A61B 18/14 |

FOREIGN PATENT DOCUMENTS

| | | |
|---|---|---|
| EP | 1977708 A1 | 10/2008 |
| EP | 3009086 A1 | 4/2016 |
| EP | 3167833 A1 | 5/2017 |
| JP | H10-085230 A | 4/1998 |
| JP | 2005-066139 A | 3/2005 |
| JP | 2005-080944 A | 3/2005 |
| JP | 2006-334068 A | 12/2006 |
| JP | 2008-253597 A | 10/2008 |
| JP | 2008-289774 A | 12/2008 |
| JP | 2012-024597 A | 2/2012 |
| KR | 2014-0100451 A | 8/2014 |
| WO | 2006/036326 A2 | 4/2006 |
| WO | 2006/064868 A1 | 6/2006 |
| WO | 2014/199759 A1 | 12/2014 |
| WO | 2016/006407 A1 | 1/2016 |

OTHER PUBLICATIONS

International Search Report dated Oct. 30, 2018 issued in PCT/JP2018/033939.

* cited by examiner

ENDOSCOPE TREATMENT TOOL

CROSS-REFERENCE TO RELATED APPLICATIONS

This is a continuation of International Application PCT/JP2018/033939, with an international filing date of Sep. 13, 2018, which is hereby incorporated by reference herein in its entirety.

TECHNICAL FIELD

The present invention relates to an endoscope treatment tool.

BACKGROUND ART

There is a known endoscope treatment tool that includes a cap that is attached to a distal end of an endoscope in an attachable/detachable manner and a high-frequency incision electrode, which protrudes forward with respect to a distal end of the cap and that laterally crosses, from left to right, the viewing field of the endoscope, and that incises tissue while observing the vicinity of the high-frequency electrode and a state of tissue in the surrounding area (for example, see Patent Literatures 1 and 2).

CITATION LIST

Patent Literature

{PTL 1} Japanese Unexamined Patent Application, Publication No. 2005-66139
{PTL 2} PCT International Publication No. 2016/006407

SUMMARY OF INVENTION

An aspect of the present invention is directed to an endoscope treatment tool including: a cylindrical distal-end member to be attached to a distal end of an endoscope; a grasping tool that is provided at an outer side surface of the endoscope along a longitudinal axis of the endoscope and that grasps biological tissue; a linear connecting member that connects the distal-end member and the grasping tool; an electrode that is disposed so as to protrude forward with respect to a distal end of the distal-end member; and an electrode driving portion that moves, in the state in which the grasping tool is grasping the biological tissue, the electrode to a position at which the biological tissue is treated, wherein the distal-end member includes holding portions that are provided at outer circumferential surfaces of the distal-end member on either side of the longitudinal axis and that secure end portions of the connecting member, the grasping tool is connected to the connecting member so that a distal end of the grasping tool can be rotated centered on the holding portions, and the electrode extends in a perpendicular direction with respect to a distal-end direction of the grasping tool and is moved, in the state in which the distal-end member is attached to the endoscope, by the electrode driving portion in a direction orthogonal to the longitudinal axis of the endoscope.

With this aspect, when the distal-end member is attached to the distal end of the endoscope, because the electrode extends in the perpendicular direction with respect to the distal-end direction of the grasping tool and is disposed in front of a distal-end surface of the distal-end member, it is possible to press the electrode against the biological tissue while observing the position of the electrode in the viewing field of the endoscope and to incise an area surrounding the biological tissue. In this case, the distal end of the grasping tool is rotated, by means of the connecting member, centered on the holding portions of the distal-end member, and the distal end of the grasping tool is brought close to the biological tissue to grasp the biological tissue with the grasping tool. Thus, in the case in which a site to be incised is, for example, above or below the current position of the electrode, due to the degree to which the biological tissue grasped by the grasping tool is elevated, it is possible to move the electrode in the viewing field of the endoscope by activating the electrode driving portion. Accordingly, it is possible to precisely align the electrode with the site to be incised without causing a change in the positional relationship between the endoscope and the tissue.

In the above-described aspect, the electrode driving portion may move the electrode in a direction along the distal-end surface of the distal-end member.

In addition, in the above-described aspect, the distal-end member may include a channel that extends in a direction along the longitudinal axis of the endoscope, the grasping tool may include an elongated insertion portion that is inserted into the channel so as to be movable in a direction along the longitudinal axis and a grasping portion that is disposed at a distal end of the insertion portion, and the connecting member may guide the grasping portion in a direction intersecting the longitudinal axis of the endoscope along an arc trajectory that is centered on an axis orthogonal to a plane including an axis of the distal-end member and an axis of the channel.

With this configuration, when the insertion portion is made to advance with respect to the channel, the grasping portion, which has been guided along the arc trajectory by the connecting member, moves in the direction intersecting the longitudinal axis of the endoscope in the viewing field of the endoscope, for example, toward the bottom from the top, and thus, it is possible to grasp tissue that is present at the bottom by the grasping portion. In this state, when the insertion portion is retracted with respect to the channel, the grasping portion moves in the viewing field of the endoscope to the top from the bottom, that is the direction intersecting the longitudinal axis of the endoscope, and thus, the tissue grasped by the grasping portion is elevated.

Because the site to be incised exists at a considerably lower portion in the initial stage of elevation, as a result of lowering the electrode in the viewing field of the endoscope by activating the electrode driving portion, it is possible to precisely align the electrode with the site to be incised without causing a change in the viewing field of the endoscope. In addition, because the site to be incised is also raised when the tissue is elevated to a high position, as a result of raising the electrode in the viewing field of the endoscope by activating the electrode driving portion, it is possible to precisely align the electrode with the site to be incised without causing a change in the viewing field of the endoscope.

In addition, in the above-described aspect, the electrode driving portion may move the electrode in the direction orthogonal to the longitudinal axis of the endoscope within a range from a bottom of the distal-end member to a height that is $2/3$ a total height.

With this configuration, because the site to be incised changes within an area from the bottom of the distal-end member to a height that is $2/3$ the total height in accordance with the degree to which the tissue is elevated, it is possible to make an incision at an appropriate position by following this change.

In addition, in the above-described aspect, the electrode have an exposed center section in a direction orthogonal to the longitudinal axis of the endoscope and orthogonal to the direction in which the electrode is moved by the electrode driving portion, and a length thereof corresponding to 20 to 80% of a total width of the distal-end member may be covered with an electrical insulation member.

With this configuration, it is possible to prevent extra tissue in the surrounding area from being incised.

In addition, in the above-described aspect, the center section in which the electrode is exposed may protrude farther forward than the insulation member does.

With this configuration, even if the electrode being covered with the insulation member abuts against the tissue, the exposed center section reliably contacts the tissue, and thus, it is possible to effectively make an incision.

In addition, in the above-described aspect, the electrode driving portion may include: a wire that connects to the electrode; an elastic member in which a distal end is secured to the distal-end member at a position on the opposite side of the grasping tool with the distal-end member sandwiched therebetween and that expands/contracts the electrode together with the wire in a direction orthogonal to the longitudinal axis of the electrode; a tube into which the wire is inserted in a movable manner; and an operating portion that is connected to a proximal end of the tube and that operates the wire so as to advance/retract the wire in a longitudinal direction.

With this configuration, as a result of an operator causing the wire to advance/retract by operating the operating portion, it is possible to move the electrode connected to the wire in the direction orthogonal to the longitudinal axis of the endoscope.

In addition, in the above-described aspect, the tube may include a flange portion secured to the electrode and a step portion provided at a position that is separated from a distal end of the tube toward the proximal end by a prescribed distance, and the elastic member may be disposed between the step portion and the flange portion.

With this configuration, when the operator pulls the wire and causes the wire to retract by operating the operating portion, the elastic member is compressed between the step portion and the flange portion, and it is possible to move the electrode in one direction in the viewing field of the endoscope; and, when the operator relaxes pulling and causes the wire to advance, the elastic member expands due to the elastic restoring force of the elastic member, and it is possible to move the electrode in the other direction, which is opposite from the one direction, in the viewing field of the endoscope.

ADVANTAGEOUS EFFECTS OF INVENTION

The present invention affords an advantage in that it is possible to precisely align an electrode at a site to be incised without causing changes in the positional relationship between an endoscope and tissue.

DESCRIPTION OF EMBODIMENT

An endoscope treatment tool 1 according to an embodiment of the present invention will be described below with reference to the drawings.

Figure 1:
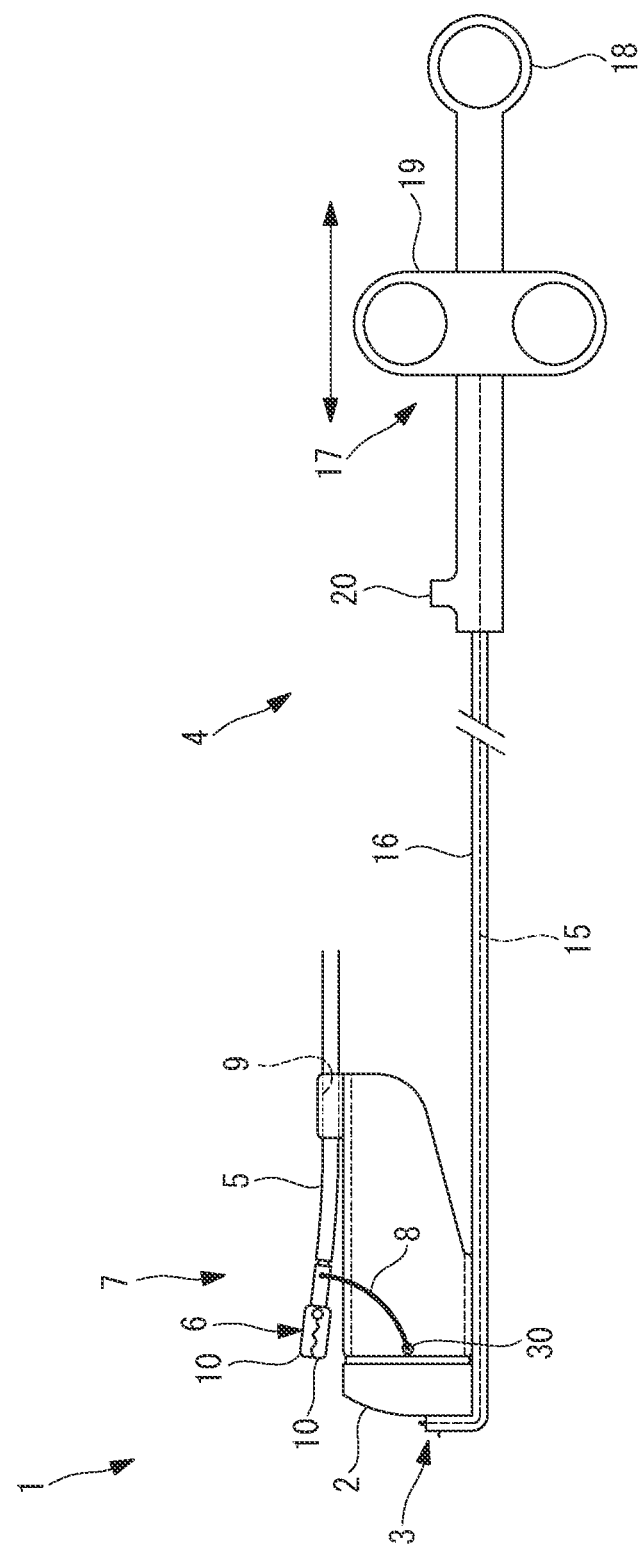
FIG. 1 is a side view showing an endoscope treatment tool according to an embodiment of the present invention.

As shown in FIG. 1, the endoscope treatment tool 1 according to this embodiment includes: a cylindrical cap (distal-end member) 2 to be attached to a distal end of an endoscope 100; a high-frequency incision electrode (electrode) 3 disposed so as to protrude forward with respect to the distal end of the cap 2; and an electrode driving portion 4 that moves the high-frequency incision electrode 3.

In the following, directions in the viewing field of the endoscope 100 when the cap 2 is attached to the distal end of the endoscope 100 will be described as top, bottom, left, and right. Specifically, the top-to-bottom direction is a direction perpendicular to the longitudinal axis of the endoscope 100, and the left-to-right direction is orthogonal to the longitudinal axis of the endoscope 100 and is orthogonal to the direction in which the high-frequency incision electrode 3 is moved by the electrode driving portion 4.

In addition, the endoscope treatment tool 1 includes: a treatment tool body (grasping tool) 7 including an elongated flexible insertion portion 5 and a treatment portion (grasping portion) 6 disposed at a distal end of the insertion portion 5; and a connecting member 8 that connects the treatment tool body 7 and the cap 2.

The cap 2 includes: a channel 9 into which the insertion portion 5 of the treatment tool body 7 is inserted so as to be movable in a longitudinal axis direction; and a holding portion 30 that secures one end of the connecting member 8.

The treatment portion 6 is, for example, grasping forceps that grasps biological tissue (see FIG. 6) X, which is a treatment target, includes a pair of grasping pieces 10 that can be opened/closed, and transmits a force applied on a proximal-end side of the insertion portion 5 to the grasping pieces 10 by means of a wire (not shown) that passes through the interior of the insertion portion 5, thus opening/closing the grasping pieces 10.

Figure 4:
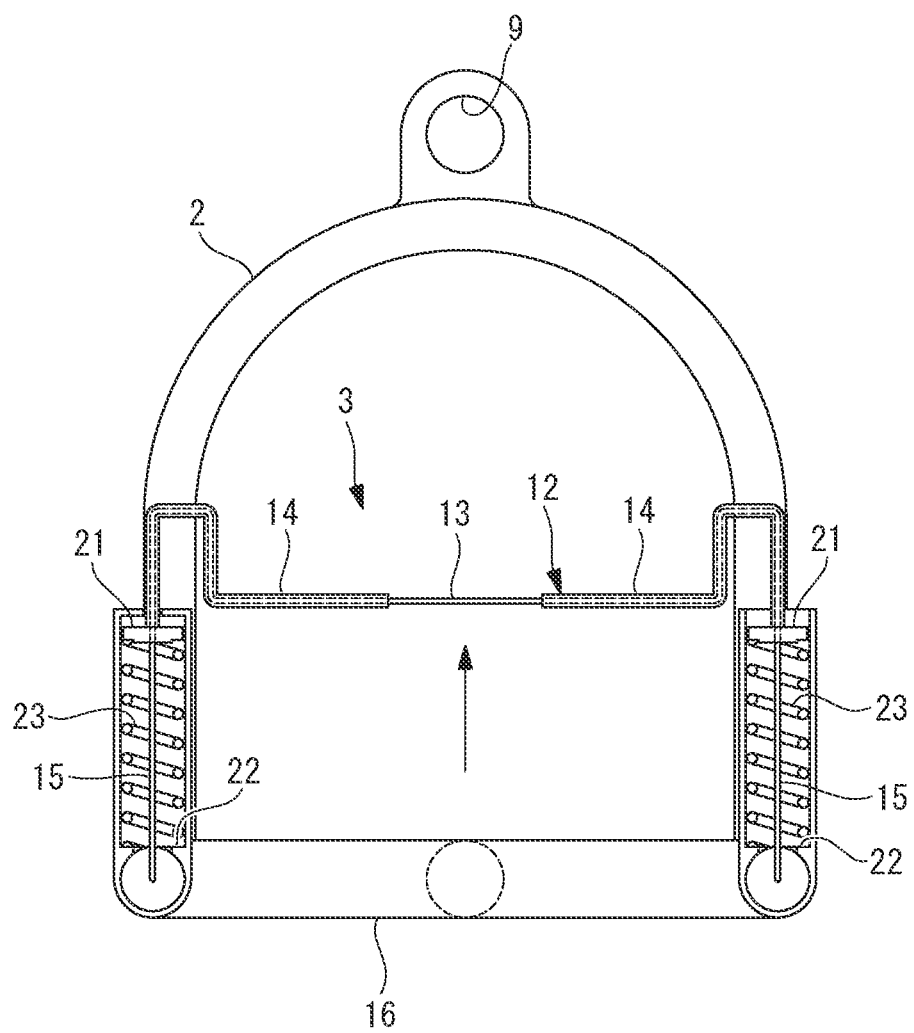
FIG. 4 is a partially cutaway front view showing the distal-end portion of the endoscope treatment tool in FIG. 1.

The cap 2 is a transparent-resin cylindrical member that is placed over the endoscope 100 from the distal end thereof in the axial direction. As shown in FIG. 4, a bottom surface of the cap 2 is flatly formed, and a top surface of the cap 2 is cylindrically formed so as to facilitate the movement of the treatment tool body 7.

The channel 9 is disposed so as to be parallel to the axis of cap 2 in the vicinity of an outer circumferential surface of a top portion of the cap 2, and has an inner diameter that allows the insertion portion 5 of the treatment tool body 7 to be inserted thereinto so as to be movable in the longitudinal axis direction.

Figure 2:
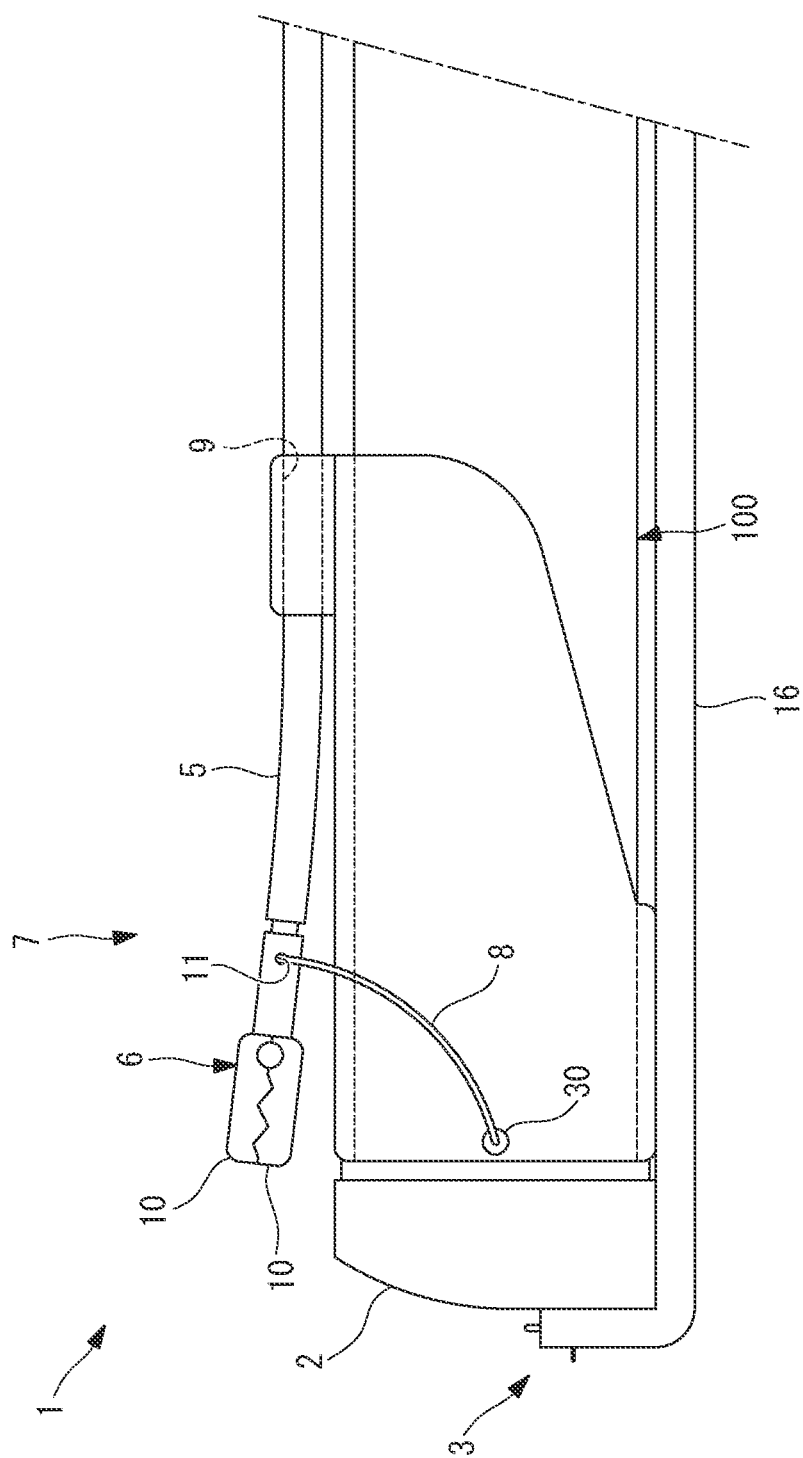
FIG. 2 is a side view showing a distal-end portion of the endoscope treatment tool in FIG. 1.

As shown in FIG. 2, the connecting member 8 is a thread, and passes through a through-hole 11 that is formed at a proximal end of the treatment portion 6 of the treatment tool body 7 in a direction orthogonal to the longitudinal axis of the insertion portion 5. Two ends of the connecting member 8 are secured at symmetrical positions on either side of the longitudinal axis of the cap 2, in other words, the two ends of the connecting member 8 are secured by the holding portions 30 that are individually provided at left and right outer circumferential surfaces of the cap 2.

Figure 3:
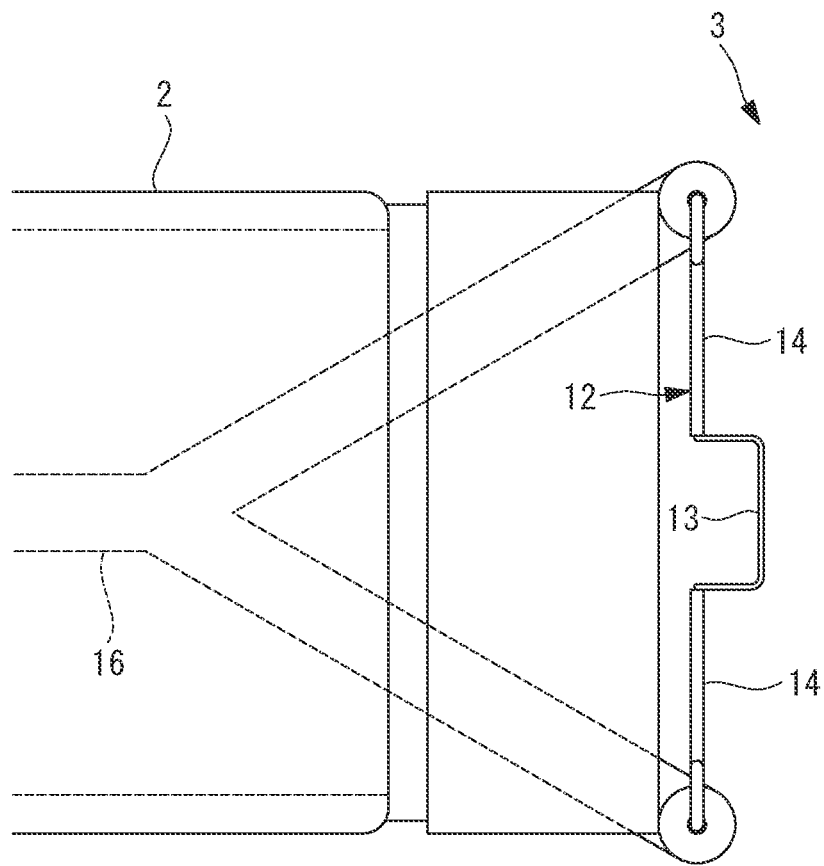
FIG. 3 is a plan view showing the distal-end portion of the endoscope treatment tool in FIG. 1.

As shown in FIGS. 3 and 4, the high-frequency incision electrode 3 includes: a rod-like electrode portion 12 that extends in the left-to-right direction in front of the cap 2; and an insulation coating (insulation member) 14 that exposes only a center portion (center section) 13 of the electrode portion 12 and covers other portions thereof, thus electrically insulating said portions. The center portion 13 of the electrode portion 12 that is exposed from the insulation coating 14 is disposed so as to be offset farther forward. In addition, two ends of the electrode portion 12 are bent and extend so as to be parallel to each other.

As shown in FIG. 1, the electrode driving portion 4 includes: a wire 15 that is electrically and mechanically connected to the electrode portion 12; an elongated tube 16 that is secured, at a distal end thereof, to a bottom side of the cap 2 and into which the wire 15 is inserted in a movable manner; and an operating portion 17 that is connected to a proximal end of the tube 16 and causes the wire 15 to be advanced/retracted in the longitudinal direction. The operating portion 17 includes: a handle 18 that is grasped by an operator; and a slider 19 that is supported so as to be linearly movable with respect to the handle 18. One end of the wire 15 is connected to the slider 19.

In the figure, reference sign 20 is a plug for connecting an external power source to the wire 15.

As shown in FIG. 3, a distal-end portion of the tube 16 is branched into two directions, that is, the left and right directions, and the respective branched portions extend in perpendicular directions with respect to the longitudinal axis of the endoscope 100 in front of the cap 2; specifically, said portions are bent upward, as shown in FIG. 2.

Figure 5:
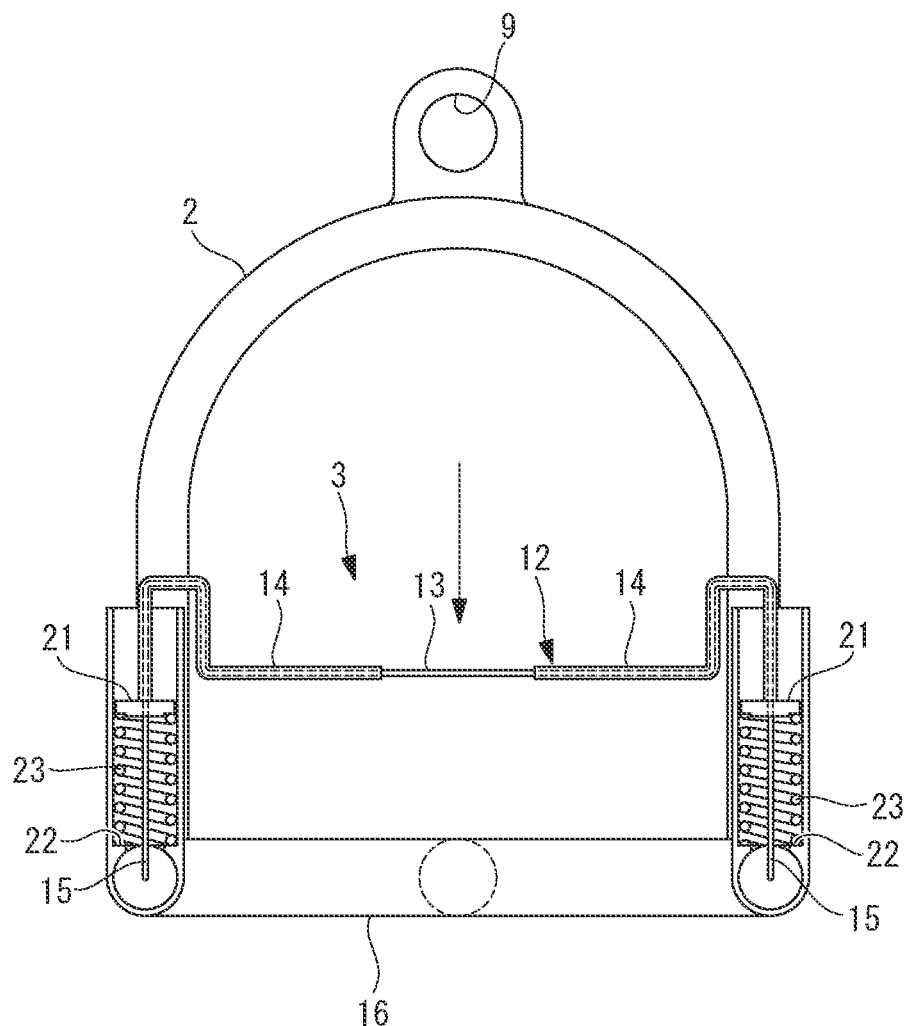
FIG. 5 is a partially cutaway front view showing a state in which a high-frequency incision electrode is lowered in the endoscope treatment tool in FIG. 4.

As shown in FIGS. 4 and 5, the tube 16 that extends upward accommodates, inside thereof: flange portions 21 that are secured at two ends of the electrode portion 12; step portions 22 that are provided inside the tube 16 at positions separated toward the proximal end from the distal end of the tube 16 by a prescribed distance; and compression springs (elastic members) 23 that are disposed between the flange portions 21 and the step portions 22. The compression springs 23 are expanded in a free state, as shown in FIG. 4, and, as a result of the wire 15 being pulled toward the proximal end by operating the operating portion 17, the compression springs 23 are compressed by this pulling force, as shown in FIG. 5.

The operation of the thus-configured endoscope treatment tool 1 according to this embodiment will be described below.

In order to execute treatment such as endoscopic submucosal dissection (ESD) or the like by employing the endoscope treatment tool 1 according to this embodiment, first, as shown in FIG. 2, the endoscope treatment tool 1 is mounted to the endoscope 100 by mounting the cap 2 to the distal end of the endoscope 100. At this time, the endoscope treatment tool 1 is mounted at an angle at which the channel 9 through which the treatment tool body 7 passes is positioned on the top side of the viewing field of the endoscope 100.

Next, the endoscope 100 to which the endoscope treatment tool 1 has been mounted is inserted into a body cavity of a patient, and is inserted until an affected part is disposed in the viewing field of the endoscope 100. Then, the angle of the endoscope 100 is adjusted to an angle at which the affected part is disposed on the bottom side of the viewing field by rotating the endoscope 100 about the longitudinal axis. Because the bottom surface of the cap 2 is flatly formed, it is possible to stably hold the endoscope 100 in the body cavity by pressing the bottom surface of the cap 2 against the mucous membrane (biological tissue) X.

Figure 6:
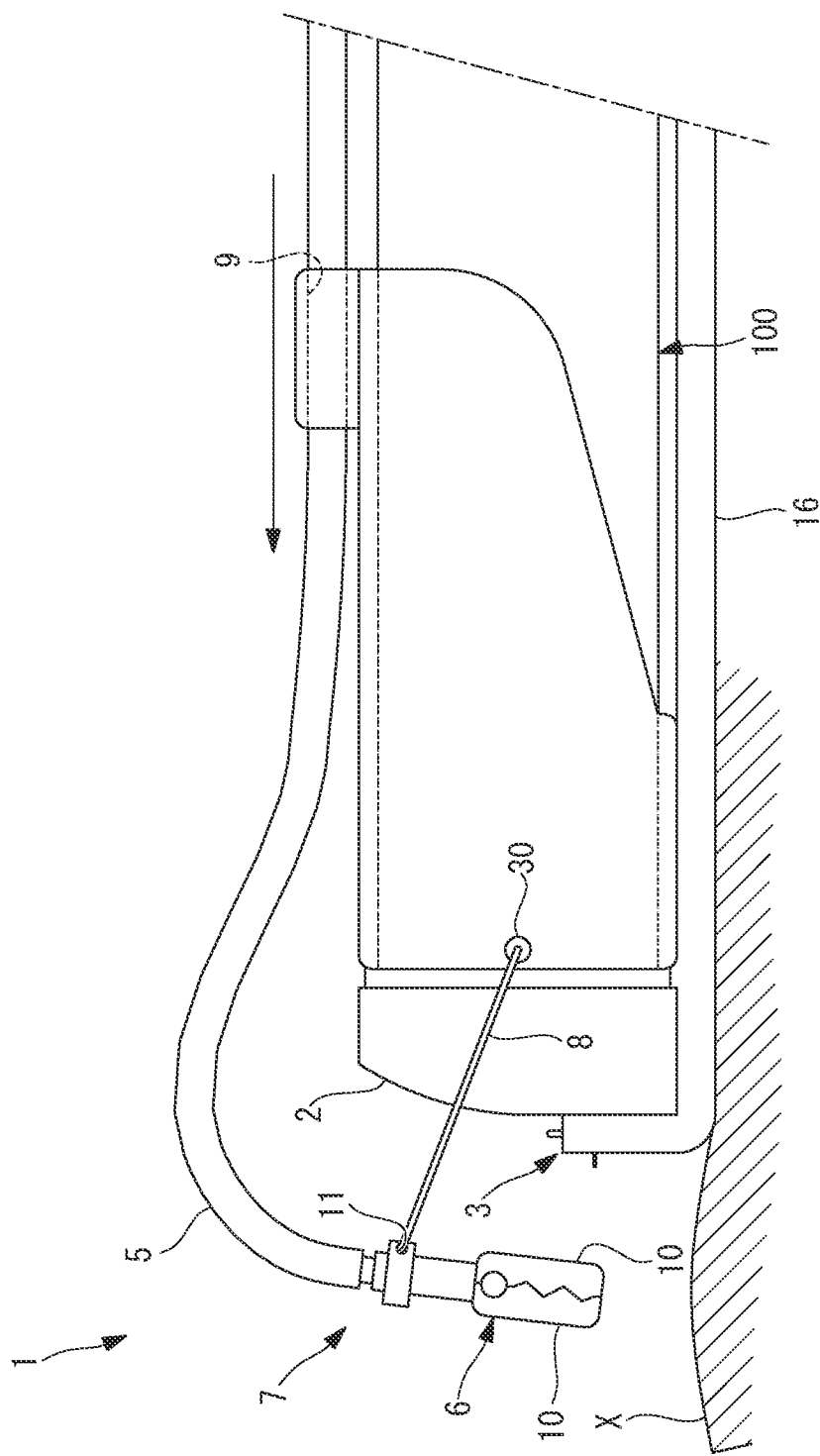
FIG. 6 is a side view showing a state in which a treatment tool body is pushed out in the endoscope treatment tool in FIG. 1.

In this state, as a result of being pushed in the direction in which the insertion portion 5 of the treatment tool body 7 is advanced, the treatment portion 6 is advanced, as shown in FIG. 6. Because the proximal end of the treatment portion 6 of the treatment tool body 7 is restrained on the cap 2 by the connecting member 8, when the insertion portion 5 is continued to be pressed in the longitudinal axis direction in a state in which the connecting member 8 is extended without slack, the treatment portion 6 is moved by the connecting member 8 along an arc trajectory in which the holding portion 30 of the cap 2 is the center of rotation until reaching a position at which the treatment portion 6 faces downward.

Figure 7:
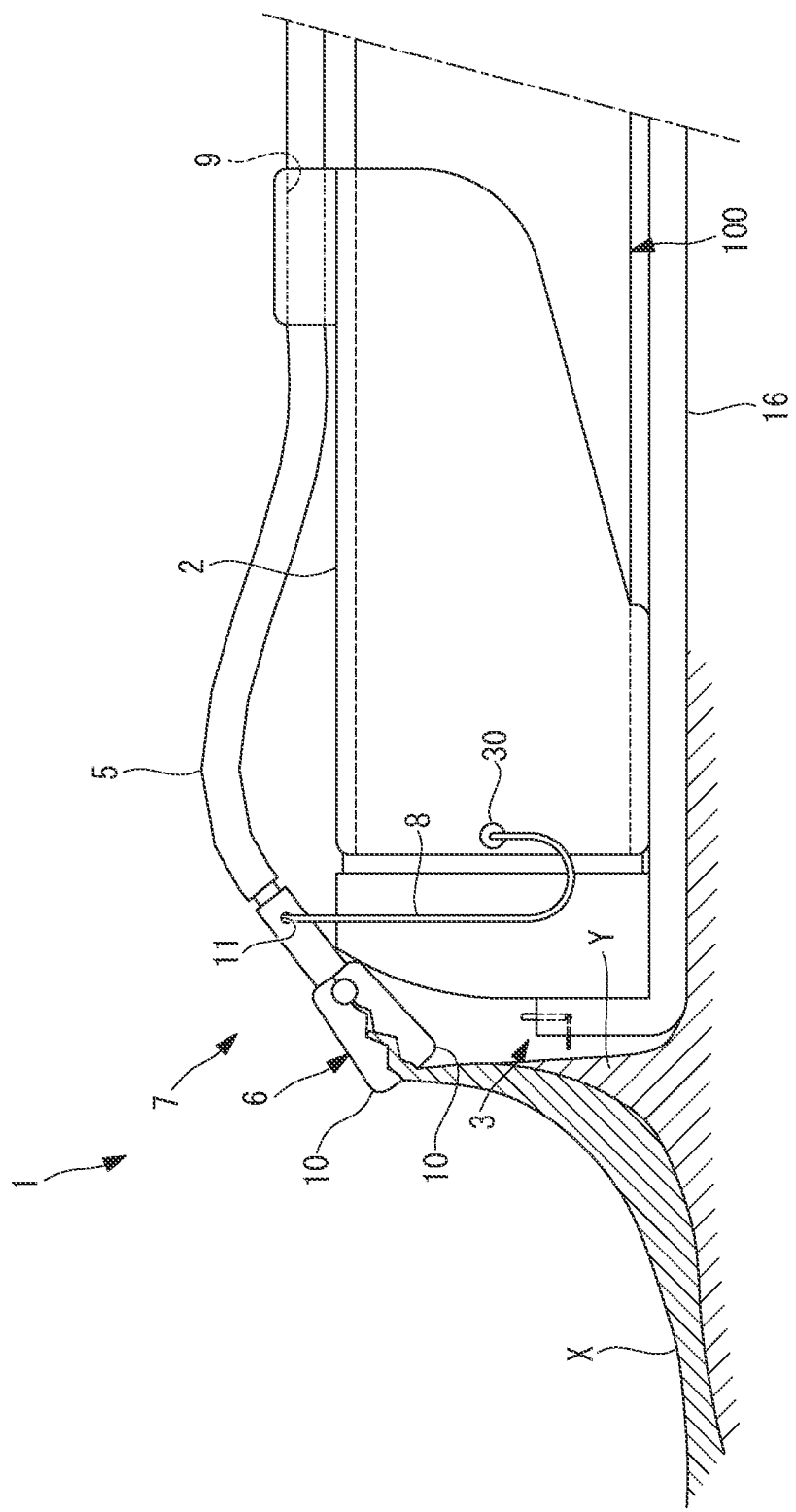
FIG. 7 is a side view showing a state in which a mucous membrane is elevated by using the treatment tool body of the endoscope treatment tool in FIG. 6.

At this position, by grasping the mucous membrane X of the affected part by opening/closing the treatment portion 6, and by pulling the insertion portion 5 to the proximal side, as shown in FIG. 7, the grasped mucous membrane X can be elevated. Because the flat bottom surface of the cap 2 is pressed against the mucous membrane X, it is possible to press down a muscle layer Y so that the muscle layer Y is not lifted when elevating the mucous membrane X.

In this state, because a sublayer of the mucous membrane X to be incised is positioned below the endoscope viewing field, the operator grasping the handle 18 pulls the wire 15 attached to the slider 19 toward the proximal end by sliding the slider 19 toward the proximal end with respect to the handle 18.

Accordingly, as a result of the flange portions 21 being pulled by the pulling force applied to the wire 15, the compression springs 23 are compressed and the electrode portion 12 is pushed down, as shown in FIG. 5. Then, in this state, by supplying power to the electrode portion 12 from the plug 20 via the wire 15, the center portion 13 being exposed from the insulation coating 14 of the electrode portion 12 is contacted with the sublayer of the mucous membrane X, and thus, it is possible to appropriately make an incision while checking the incision position by using an endoscope image.

Figure 8:
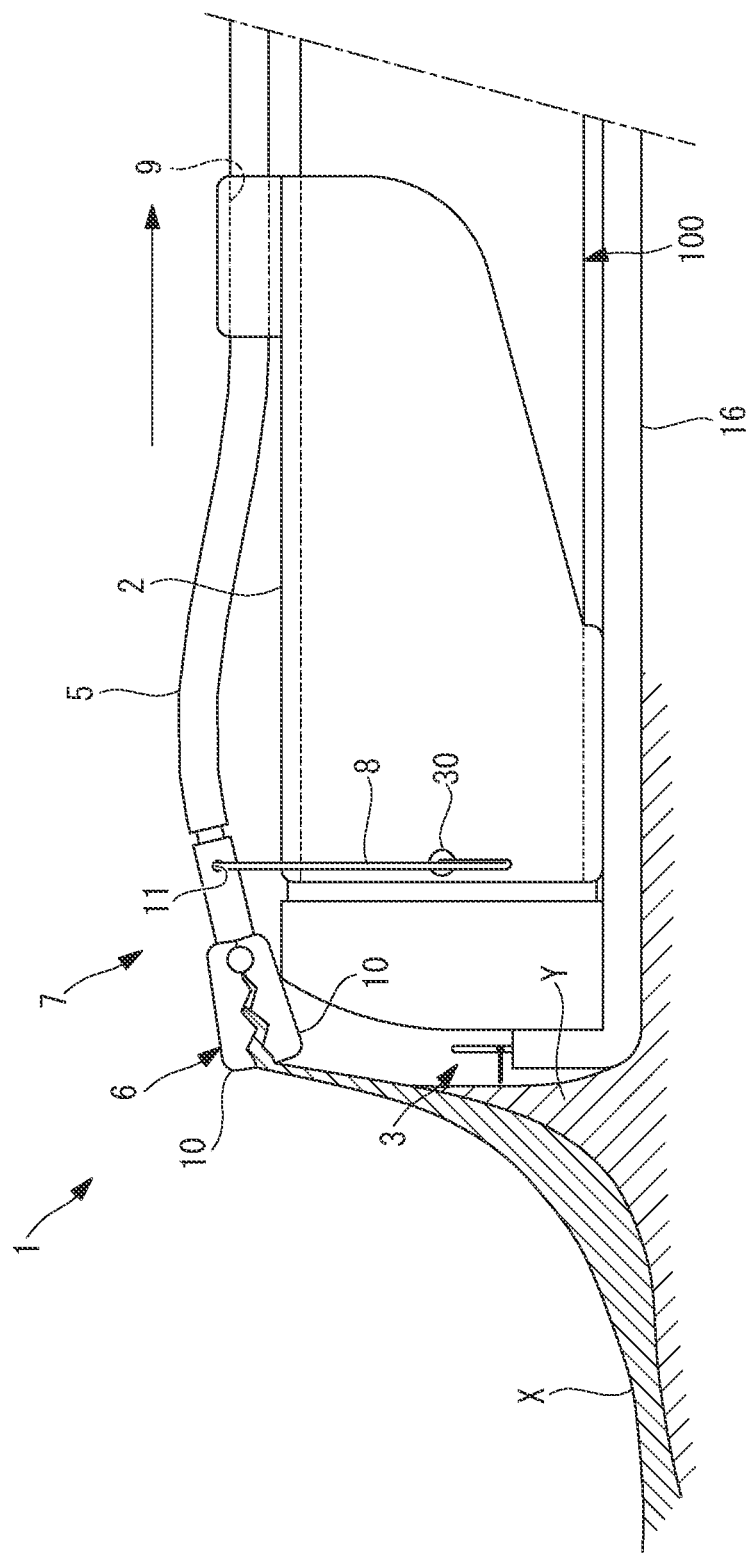
FIG. 8 is a side view showing the state in which the mucous membrane is further elevated by using the treatment tool body of the endoscope treatment tool in FIG. 7.

In addition, as shown in FIGS. 7 and 8, the position at which an incision is to be made moves in the top-to-bottom direction depending on the degree to which the mucous membrane X is elevated by the treatment tool body 7. In this case also, with the endoscope treatment tool 1 according to this embodiment, as a result of relaxing the pulling force being applied to the slider 19 in the operating portion 17, it is possible to raise the electrode portion 12, as shown in FIGS. 4 and 8, by expanding the compression springs 23 by means of elastic restoring forces, and thus, it is possible to adjust the position at which an incision is to be made.

As has been described above, with the endoscope treatment tool 1 according to this embodiment, it is possible to move the electrode portion 12, which is disposed in front of the endoscope 100, upward and downward without causing a change in the viewing field of the endoscope 100, and thus, there is an advantage in that it is possible to appropriately adjust the electrode portion 12 of the high-frequency incision electrode 3 with respect to the position at which an incision is to be made, and thus, it is possible to apply treatment at a desired position.

In addition, in this embodiment, because the high-frequency incision electrode 3 is covered with the insulation coating 14, with only the center portion 13 of the rod-like electrode portion 12 being exposed, it is possible to selectively incise a desired site, and it is possible to prevent in advance the occurrence of a problem in which an unnecessary portion is incised. In this case, the length of the region in which the electrode portion 12 is exposed may be 20 to 80% of the lateral width of the cap 2.

In addition, because the electrode portion 12 exposed from the insulation coating 14 is offset forward, it is possible to make the electrode portion 12, which actually performs incision, contact the biological tissue X without causing the biological tissue X to interfere with the other portions of the high-frequency incision electrode 3.

In addition, it is preferable that the area in which the high-frequency incision electrode 3 is moved upward and downward by the electrode driving portion 4 be an area from the bottom surface of the cap 2 to a height that is ⅔ the total height in a direction orthogonal to the longitudinal direction of the endoscope 100. Because the site to be incised changes in the area from the bottom of the cap 2 to the height that is ⅔ the total height depending on the degree to which the biological tissue X is elevated, it is possible to make an incision at an appropriate position by following this change.

In addition, although the high-frequency incision electrode 3 is assumed to be moved upward and downward as a result of the electrode driving portion 4 pulling the wire 15 for energizing the high-frequency incision electrode 3, alternatively, the high-frequency incision electrode 3 may be moved upward and downward by means of other arbitrary methods.

Figure 9:
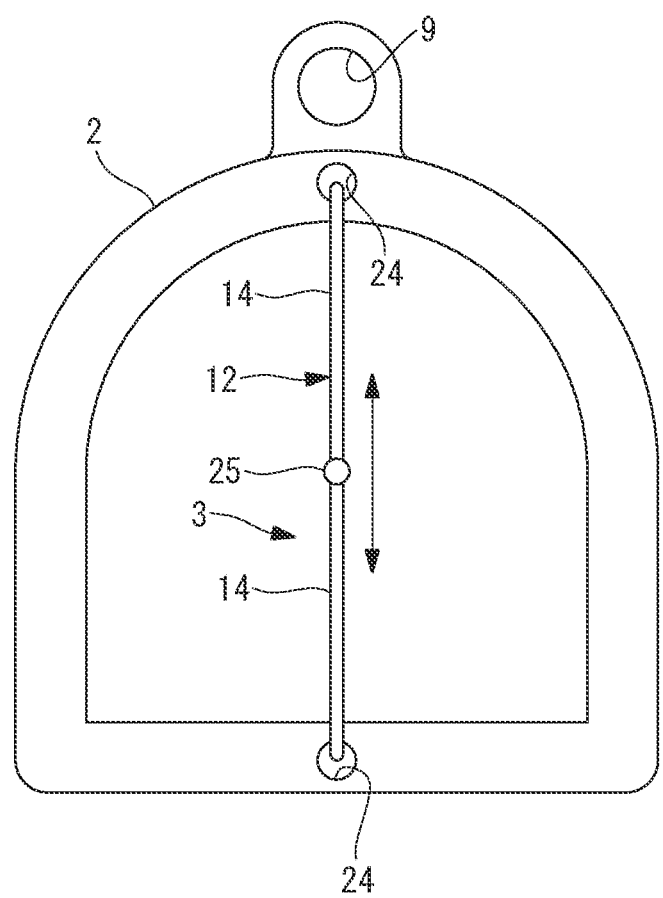
FIG. 9 is a front view showing a modification of the endoscope treatment tool in FIG. 1.

In addition, for example, as shown in FIG. 9, a wire-like high-frequency incision electrode 3, in which only a portion of an exposed portion 25 is exposed from the insulation coating 14, may be inserted into through-holes 24 provided at the top and the bottom of the cap 2 along the axial direction, and the exposed portion 25 may be moved upward and downward by pushing one of top and bottom end portions toward the distal end and by pulling the other end portion toward the proximal end.

As a result, the above-described embodiment leads to the following aspect.

An aspect of the present invention is directed to an endoscope treatment tool including: a cylindrical distal-end member to be attached to a distal end of an endoscope; a grasping tool that is provided at an outer side surface of the endoscope along a longitudinal axis of the endoscope and that grasps biological tissue; a linear connecting member that connects the distal-end member and the grasping tool; an electrode that is disposed so as to protrude forward with respect to a distal end of the distal-end member; and an electrode driving portion that moves, in the state in which the grasping tool is grasping the biological tissue, the electrode to a position at which the biological tissue is treated, wherein the distal-end member includes holding portions that are provided at outer circumferential surfaces of the distal-end member on either side of the longitudinal axis and that secure end portions of the connecting member, the grasping tool is connected to the connecting member so that a distal end of the grasping tool can be rotated centered on the holding portions, and the electrode extends in a perpendicular direction with respect to a distal-end direction of the grasping tool and is moved, in the state in which the distal-end member is attached to the endoscope, by the electrode driving portion in a direction orthogonal to the longitudinal axis of the endoscope.

With this aspect, when the distal-end member is attached to the distal end of the endoscope, because the electrode extends in the perpendicular direction with respect to the distal-end direction of the grasping tool and is disposed in front of a distal-end surface of the distal-end member, it is possible to press the electrode against the biological tissue while observing the position of the electrode in the viewing field of the endoscope and to incise an area surrounding the biological tissue. In this case, the distal end of the grasping tool is rotated, by means of the connecting member, centered on the holding portions of the distal-end member, and the distal end of the grasping tool is brought close to the biological tissue to grasp the biological tissue with the grasping tool. Thus, in the case in which a site to be incised is, for example, above or below the current position of the electrode, due to the degree to which the biological tissue grasped by the grasping tool is elevated, it is possible to move the electrode in the viewing field of the endoscope by activating the electrode driving portion. Accordingly, it is possible to precisely align the electrode with the site to be incised without causing a change in the positional relationship between the endoscope and the tissue.

In the above-described aspect, the electrode driving portion may move the electrode in a direction along the distal-end surface of the distal-end member.

In addition, in the above-described aspect, the distal-end member may include a channel that extends in a direction along the longitudinal axis of the endoscope, the grasping tool may include an elongated insertion portion that is inserted into the channel so as to be movable in a direction along the longitudinal axis and a grasping portion that is disposed at a distal end of the insertion portion, and the connecting member may guide the grasping portion in a direction intersecting the longitudinal axis of the endoscope along an arc trajectory that is centered on an axis orthogonal to a plane including an axis of the distal-end member and an axis of the channel.

With this configuration, when the insertion portion is made to advance with respect to the channel, the grasping portion, which has been guided along the arc trajectory by the connecting member, moves in the direction intersecting the longitudinal axis of the endoscope in the viewing field of the endoscope, for example, toward the bottom from the top, and thus, it is possible to grasp tissue that is present at the bottom by the grasping portion. In this state, when the insertion portion is retracted with respect to the channel, the grasping portion moves in the viewing field of the endoscope to the top from the bottom, that is the direction intersecting the longitudinal axis of the endoscope, and thus, the tissue grasped by the grasping portion is elevated.

Because the site to be incised exists at a considerably lower portion in the initial stage of elevation, as a result of lowering the electrode in the viewing field of the endoscope by activating the electrode driving portion, it is possible to precisely align the electrode with the site to be incised without causing a change in the viewing field of the endoscope. In addition, because the site to be incised is also raised when the tissue is elevated to a high position, as a result of raising the electrode in the viewing field of the endoscope by activating the electrode driving portion, it is possible to precisely align the electrode with the site to be incised without causing a change in the viewing field of the endoscope.

In addition, in the above-described aspect, the electrode driving portion may move the electrode in the direction orthogonal to the longitudinal axis of the endoscope within a range from a bottom of the distal-end member to a height that is ⅔ a total height.

With this configuration, because the site to be incised changes within an area from the bottom of the distal-end member to a height that is ⅔ the total height in accordance with the degree to which the tissue is elevated, it is possible to make an incision at an appropriate position by following this change.

In addition, in the above-described aspect, the electrode have an exposed center section in a direction orthogonal to the longitudinal axis of the endoscope and orthogonal to the direction in which the electrode is moved by the electrode driving portion, and a length thereof corresponding to 20 to 80% of a total width of the distal-end member may be covered with an electrical insulation member.

With this configuration, it is possible to prevent extra tissue in the surrounding area from being incised.

In addition, in the above-described aspect, the center section in which the electrode is exposed may protrude farther forward than the insulation member does.

With this configuration, even if the electrode being covered with the insulation member abuts against the tissue, the exposed center section reliably contacts the tissue, and thus, it is possible to effectively make an incision.

In addition, in the above-described aspect, the electrode driving portion may include: a wire that connects to the electrode; an elastic member in which a distal end is secured to the distal-end member at a position on the opposite side of the grasping tool with the distal-end member sandwiched therebetween and that expands/contracts the electrode together with the wire in a direction orthogonal to the longitudinal axis of the electrode; a tube into which the wire is inserted in a movable manner; and an operating portion that is connected to a proximal end of the tube and that operates the wire so as to advance/retract the wire in a longitudinal direction.

With this configuration, as a result of an operator causing the wire to advance/retract by operating the operating portion, it is possible to move the electrode connected to the wire in the direction orthogonal to the longitudinal axis of the endoscope.

In addition, in the above-described aspect, the tube may include a flange portion secured to the electrode and a step portion provided at a position that is separated from a distal end of the tube toward the proximal end by a prescribed distance, and the elastic member may be disposed between the step portion and the flange portion.

With this configuration, when the operator pulls the wire and causes the wire to retract by operating the operating portion, the elastic member is compressed between the step portion and the flange portion, and it is possible to move the electrode in one direction in the viewing field of the endoscope; and, when the operator relaxes pulling and causes the wire to advance, the elastic member expands due to the elastic restoring force of the elastic member, and it is possible to move the electrode in the other direction, which is opposite from the one direction, in the viewing field of the endoscope.

The present invention affords an advantage in that it is possible to precisely align an electrode at a site to be incised without causing changes in the positional relationship between an endoscope and tissue.

REFERENCE SIGNS LIST 1 endoscope treatment tool
2 cap (distal-end member)
3 high-frequency incision electrode (electrode)
4 electrode driving portion
5 insertion portion
6 treatment portion (grasping portion)
7 treatment tool body (grasping tool)
8 connecting member
9 channel
13 center portion (center section)
14 insulation coating (insulation member)
15 wire
16 tube
17 operating portion
21 flange portion
22 step portion
23 compression spring (elastic member)
30 holding portion
100 endoscope
X mucous membrane (biological tissue)

The invention claimed is:

1. An endoscope treatment tool comprising:
a cylindrical distal-end member configured to be attached to a distal end of an endoscope;
a grasping tool provided at a first side of the distal-end member relative to a longitudinal axis of the endoscope and extending on an outer side surface of the endoscope along the longitudinal axis of the endoscope, a distal portion of the grasping tool is configured to grasp biological tissue, and is movable in a first direction away from the first side and in a second direction toward from the first side;
an electrode protruding distally from a distal face of the distal-end member; and
an electrode driving portion configured to move the electrode in the first direction and in the second direction, the electrode driving portion comprising:
a tube, a distal end of the tube is fixed to a second side of the distal-end member, the second side is opposed to the first side relative to the longitudinal axis;
a wire movably disposed within the tube, the wire connected to the electrode for moving the electrode in one of the first direction and the second direction; and
an elastic member disposed at a distal end of the distal-end member between the first side and the second side, the elastic member biasing the electrode in an other of the first direction and the second direction.

2. The endoscope treatment tool according to claim 1, further comprising:
a linear connecting member that connects the distal-end member and the grasping tool,
wherein the distal-end member includes holding portions that are provided at outer circumferential surfaces of the distal-end member on either side of the longitudinal axis and that secure end portions of the distal-end member,
the grasping tool is connected to the connecting member so that a distal end of the grasping tool is rotatable centered on the holding portions, and the first direction and the second direction are orthogonal to the longitudinal axis of the endoscope.

3. The endoscope treatment tool according to claim 2, wherein
the distal-end member comprises a channel that extends in a direction along the longitudinal axis of the endoscope,
the grasping tool comprises an elongated insertion portion that is inserted into the channel so as to be movable in the direction along the longitudinal axis and a grasping portion that is disposed at the distal portion of the insertion portion, and
the connecting member guides the grasping portion in the first direction along an arc trajectory centered on an axis orthogonal to the longitudinal axis.

4. The endoscope treatment tool according to claim 2, wherein the electrode driving portion moves the electrode in the first direction within a range from a bottom of the distal-end member to a height that is ⅔ a total height.

5. The endoscope treatment tool according to claim 2, wherein the electrode has an exposed center section in the direction orthogonal to the longitudinal axis of the endoscope, and a length of the electrode corresponding to 20 to 80% of a total width of the distal-end member is covered with an electrical insulation member.

6. The endoscope treatment tool according to claim 5, wherein the center section in which the electrode is exposed protrudes farther forward than the insulation member does.

7. The endoscope treatment tool according to claim 1, wherein the electrode driving portion comprises: an operating portion that is connected to a proximal end of the tube and that operates the wire so as to advance/retract the wire in a longitudinal direction.

8. The endoscope treatment tool according to claim 7, wherein
the electrode comprises a flange portion secured to the electrode and the tube comprises a step portion provided at a position that is separated from the flange portion, and
the elastic member is disposed between the step portion and the flange portion.

* * * * *